United States Patent [19]

David et al.

[11] Patent Number: 5,478,572
[45] Date of Patent: Dec. 26, 1995

[54] GEPIRONE DOSAGE FORM

[75] Inventors: Stephen T. David, Evansville; Claude E. Gallian, Newburgh, both of Ind.; Joseph C. H. Chou, Downington, Pa.

[73] Assignee: Bristol-Myers Squibb Co., New York, N.Y.

[21] Appl. No.: 301,281

[22] Filed: Sep. 6, 1994

[51] Int. Cl.⁶ .......................... A61K 31/505; A61K 9/52; A61K 9/26
[52] U.S. Cl. .......................... 424/468; 424/469; 424/470; 424/474; 424/480; 424/484; 424/488; 424/494; 514/252; 514/256; 514/963; 514/964; 514/965
[58] Field of Search .......................... 514/252, 256, 514/963, 964, 965; 424/468, 469, 470, 474, 480, 484, 488, 494

[56] References Cited

U.S. PATENT DOCUMENTS

| | | | |
|---|---|---|---|
| 3,870,790 | 3/1975 | Lowey et al. | 421/19 |
| 3,965,256 | 6/1976 | Leslie | 424/22 |
| 4,226,849 | 10/1980 | Schor | 424/19 |
| 4,235,870 | 11/1980 | Leslie | 424/19 |
| 4,248,856 | 2/1981 | Guley et al. | 424/21 |
| 4,248,858 | 2/1981 | Guley et al. | 424/21 |
| 4,309,406 | 1/1982 | Guley et al. | 424/21 |
| 4,357,469 | 11/1982 | Schor | 536/91 |
| 4,369,172 | 1/1983 | Schor et al. | 424/19 |
| 4,389,393 | 6/1983 | Schor et al. | 424/19 |
| 4,415,547 | 11/1983 | Yu et al. | 424/19 |
| 4,423,049 | 12/1983 | Temple | 424/251 |
| 4,547,358 | 10/1985 | David et al. | 514/263 |
| 4,610,870 | 9/1986 | Jain et al. | 424/19 |
| 4,690,824 | 9/1987 | Powell et al. | 424/468 |
| 4,695,591 | 9/1987 | Hanna et al. | 514/781 |
| 4,704,284 | 11/1987 | Beatty et al. | 421/469 |
| 4,771,053 | 9/1988 | Cott et al. | 514/256 |
| 4,782,060 | 11/1988 | Kurtz et al. | 514/252 |
| 4,942,040 | 7/1990 | Ragnarsson et al. | 424/486 |
| 4,981,695 | 1/1991 | Appelgren et al. | 424/456 |
| 5,096,908 | 3/1992 | Gidda et al. | 514/307 |
| 5,106,849 | 4/1992 | Abou-Gharbia et al. | 514/252 |
| 5,124,346 | 6/1992 | Seymour | 514/397 |
| 5,169,638 | 12/1992 | Dennis et al. | 424/457 |
| 5,292,766 | 3/1994 | Clemens | 514/415 |
| 5,378,846 | 1/1995 | Seredenin et al. | 514/249 |
| 5,387,604 | 2/1995 | McDonald et al. | 514/456 |

OTHER PUBLICATIONS

Ford et al., "Importance of drug type, tablet shape and added diluents on drug release kinetics from hydroxypropylmethylcellulose matrix tablets", *International Journal of Pharmaceuticals*, 40 pp. 223–224 (1987).

*Primary Examiner*—Ronald W. Griffin
*Attorney, Agent, or Firm*—Sandra M. Nolan

[57] ABSTRACT

Gepirone compositions having extended release properties contain a gepirone salt, a cellulosic polymer matrix and suitable quantities of pharmaceutical excipients. Dosage forms based thereon require 18 to 24 hours for release of 90 to 95% of gepirone.

16 Claims, 4 Drawing Sheets

GEPIRONE DOSAGE FORM

FIELD OF THE INVENTION

The invention relates to an extended release formulation, preferably in the form of a tablet or other oral dosage form, for slowly releasing the medicinal agent, gepirone.

BACKGROUND OF INVENTION

Gepirone and its salts are antidepressant and anxiolytic agents. They are typically used to treat depression, dysthymia, impulse disorders, panic attacks and the like. Gepirone has a short half-life when orally administered in immediate-release formulations. Its time to maximum drug concentration in the bloodstream (Tmax) is about 1 hour and its T-50 (i.e. time until 50% of the drug has been released under controlled in vitro conditions) is about 2.5°3 hours. Because of its rapid metabolism, gepirone has been administered in the past in several small dosages—e.g., 5 to 10 rag. doses, 2 to 3 times per day. This multiple dosing scheme can lead to compliance problems. Failure to take the second or third dose results in unacceptably low plasma levels of gepirone.

Also, studies indicate that, for 15 to 20 hours after administration, oral immediate release gepirone formulations can yield significant variations in human plasma concentrations.

Gepirone has the names:
(1) 4,4-dimethyl-1-[4-[4-(2-pyrimidinyl)-1-piperazinyl]butyl]-2,6-piperidinedione, and
(2) 3,3-dimethyl-1-[4-[4-(2-pyrimidinyl)-1-piperazinyl]butyl]-glutarimide.

It can be effectively administered using its hydrochloride salt, gepirone hydrochloride (gepirone HCl). The preparation of gepirone hydrochloride is described in Example 7 of U.S. Pat. No. 4,423,049 to D. L. Temple et al.

Gepirone's principal metabolite is 1-(2-pyrimidinyl)piperazine (1-PP). The release of 1-PP is believed to be responsible for adverse side effects. Such side effects include dizziness, nausea, headache and drowsiness.

SUMMARY OF INVENTION

It has been discovered that gepirone can be orally administered in once-a-day extended release (ER) dosage forms which contain gepirone hydrochloride, a cellulosic polymer matrix and suitable amounts of pharmaceutical excipients. The resultant gepirone ER formulations yield oral products which require about 19 to about 24 hours to release 90 to 95% of the active agent, gepirone.

The invention deals with these formulations, dosage forms based thereon, and methods for the preparation and use of both.

The experimental procedures used to generate the data shown are discussed in more detail infra.

DETAILED DESCRIPTION OF THE INVENTION

The composition, dosage forms and methods of the invention have several advantages over immediate-release gepirone systems.

Patient compliance is better because the ER dosage forms need be taken only once in a 24-hour period. Thus, plasma concentration levels do not vary unacceptably—i.e., give high initial drug levels that are associated with the incidence of unwanted side effects, as well as having rapid drops in drug levels to below therapeutic levels—when the ER dosage forms are administered.

As a second advantage, the side effects generally associated with high metabolite (i.e. 1-PP) levels are minimal with the ER product.

As another aspect of the invention, certain tablets made in accordance with the invention have an oval shape, which enhances their surface area and improves the release of gepirone therefrom.

In representative embodiments, an extended release oral dosage form for gepirone administration contains, in weight percents:

(a) about 0.6 to about 10.7% gepirone hydrochloride,
(b) about 72.7 about to 82.1% hydroxypropylmethylcellulose having a viscosity of from about 15,000 to about 100,000 cps.,
(c) about 0 to about 0.3% iron oxide,
(d) about 11.0 to about 16.7% microcrystalline cellulose,
(e) about 0.42 to about 0.47% colloidal silica, and
(f) about 0.3 to about 1.0% magnesium stearate.

Figure 1:
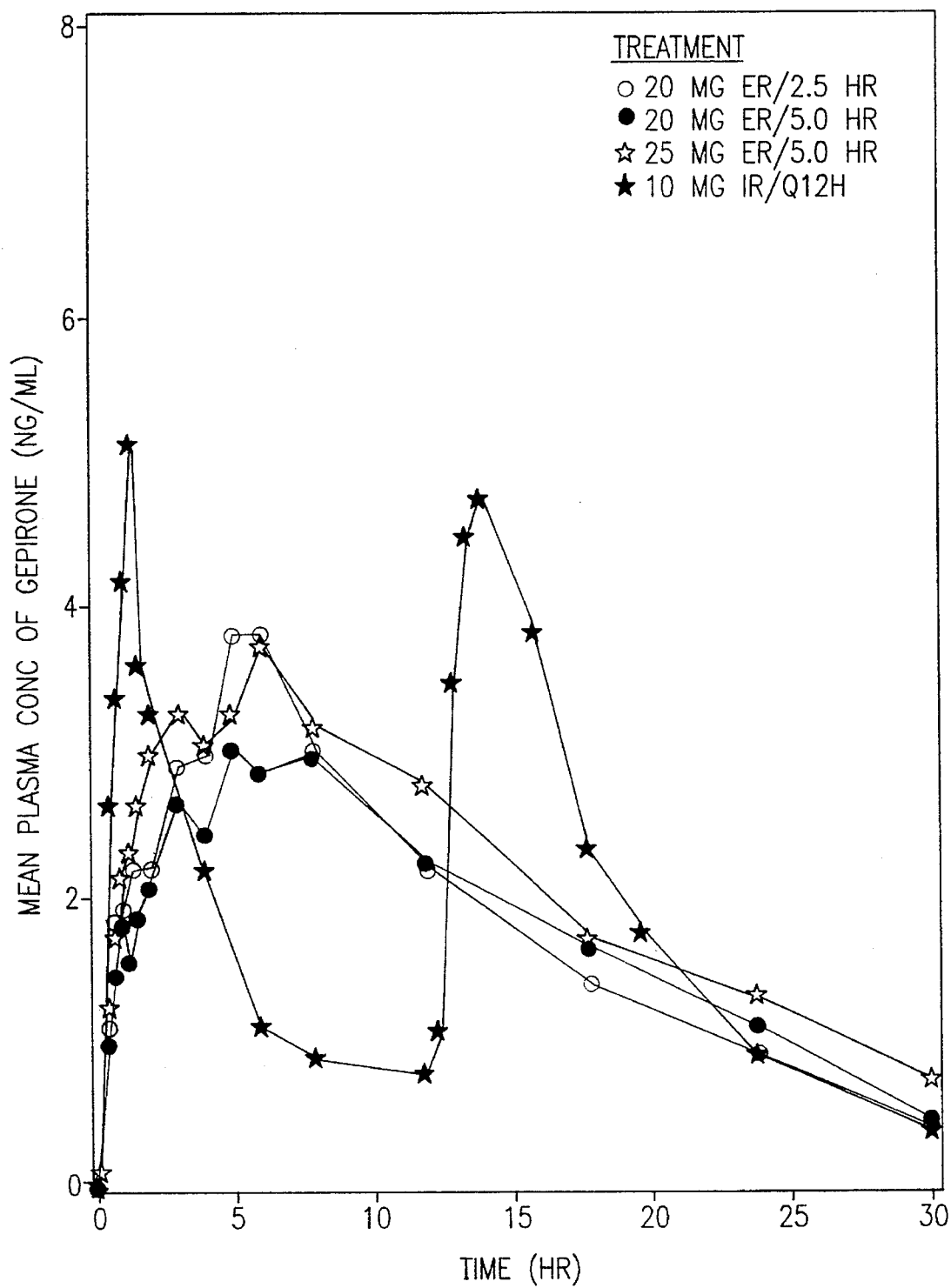
FIG. 1 is a plot of the mean plasma level of the active agent, gepirone, versus time for the dose regimens specified.
Figure 2:
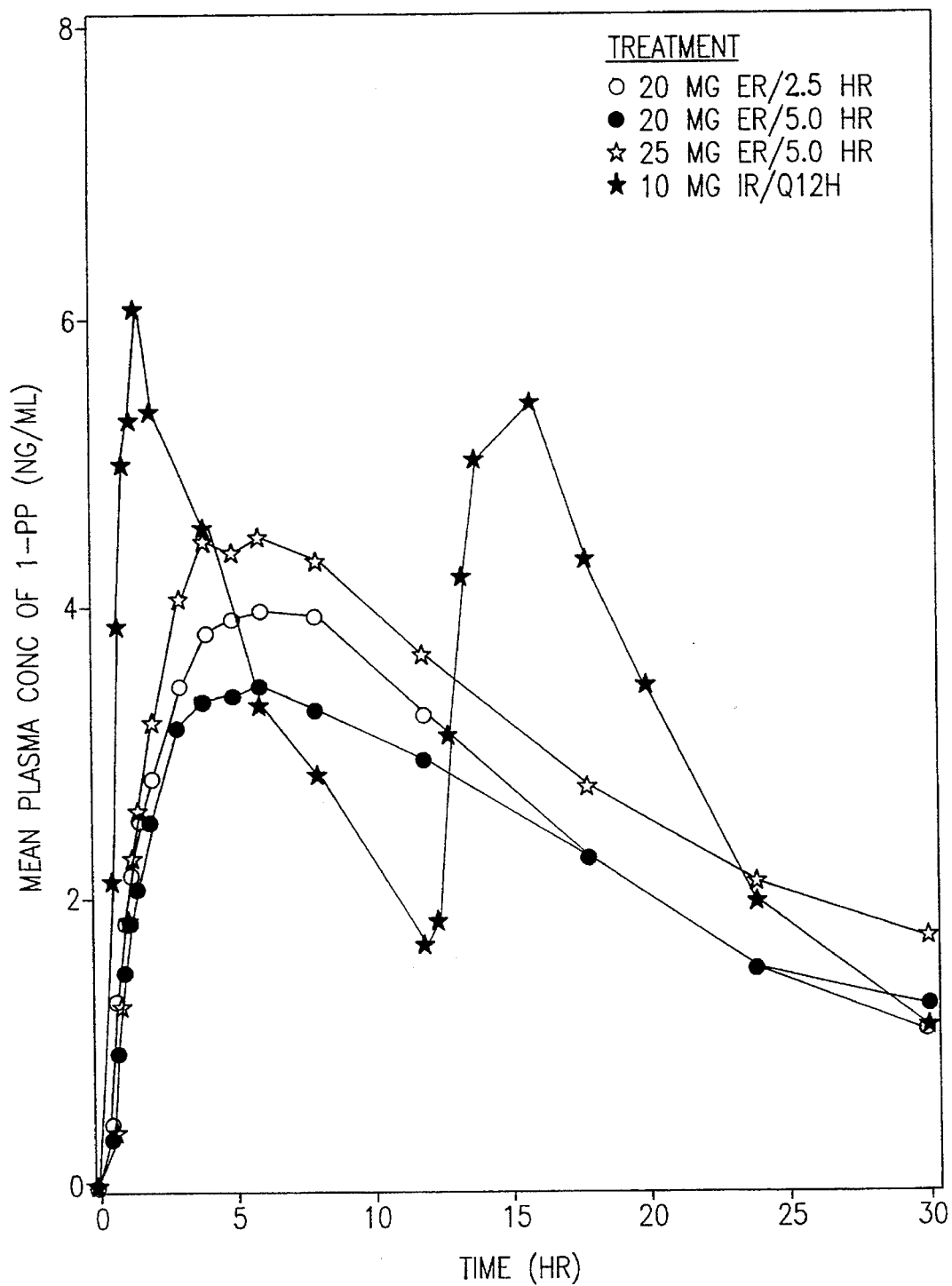
FIG. 2 is a graph showing mean plasma concentrations of gepirone's principle metabolite, 1-(2-pyrimidinyl)piperazine (1-PP), versus time for the dose regimens specified.

As FIGS. 1 and 2 indicate, the mean plasma concentrations of gepirone and 1-PP in man after ingesting oral gepirone have been plotted against time. Comparison of these plots indicates that, overall, plasma levels of the 1-PP metabolite are somewhat higher than levels of gepirone. It is noteworthy, then, that the incidence of side effects associated with high 1-PP levels decreases when gepirone ER is ingested.

When ER gepirone was orally administered to human subjects, Tmax averaged about 4.8 to about 5.6 hours. Compare these values to an average IR dosage Tmax value of about 1.3 hours.

Figure 3:
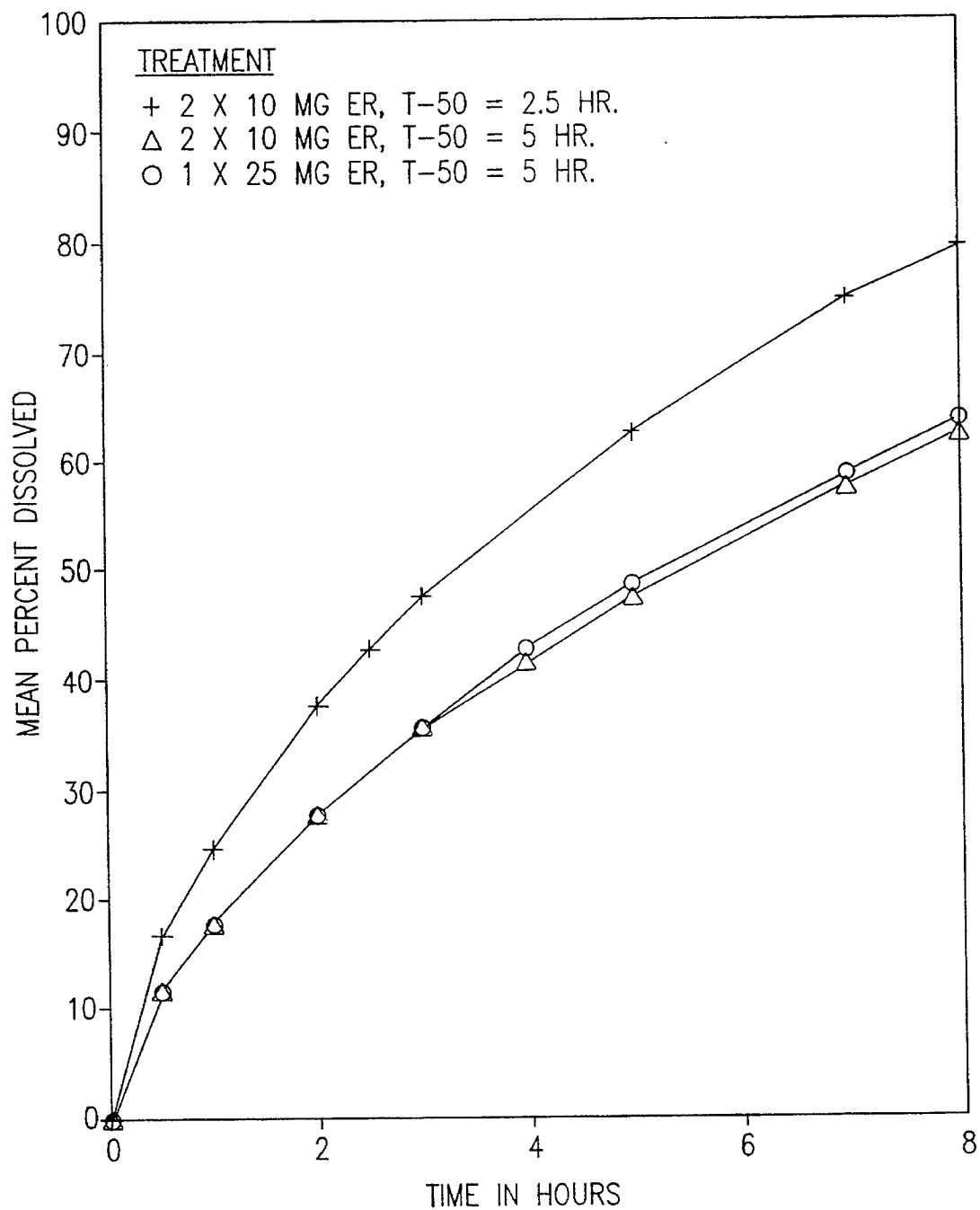
FIG. 3 shows, for the three treatments indicated, percent drug dissolved in vitro, plotted against time following administration (8 hours maximum).

FIG. 3 shows in vitro drug dissolution profiles over 8 hours. Note that significant solution gepirone levels result in 30 minutes, with 60 to 80% release of drug into solution in 8 hours.

Figure 4:
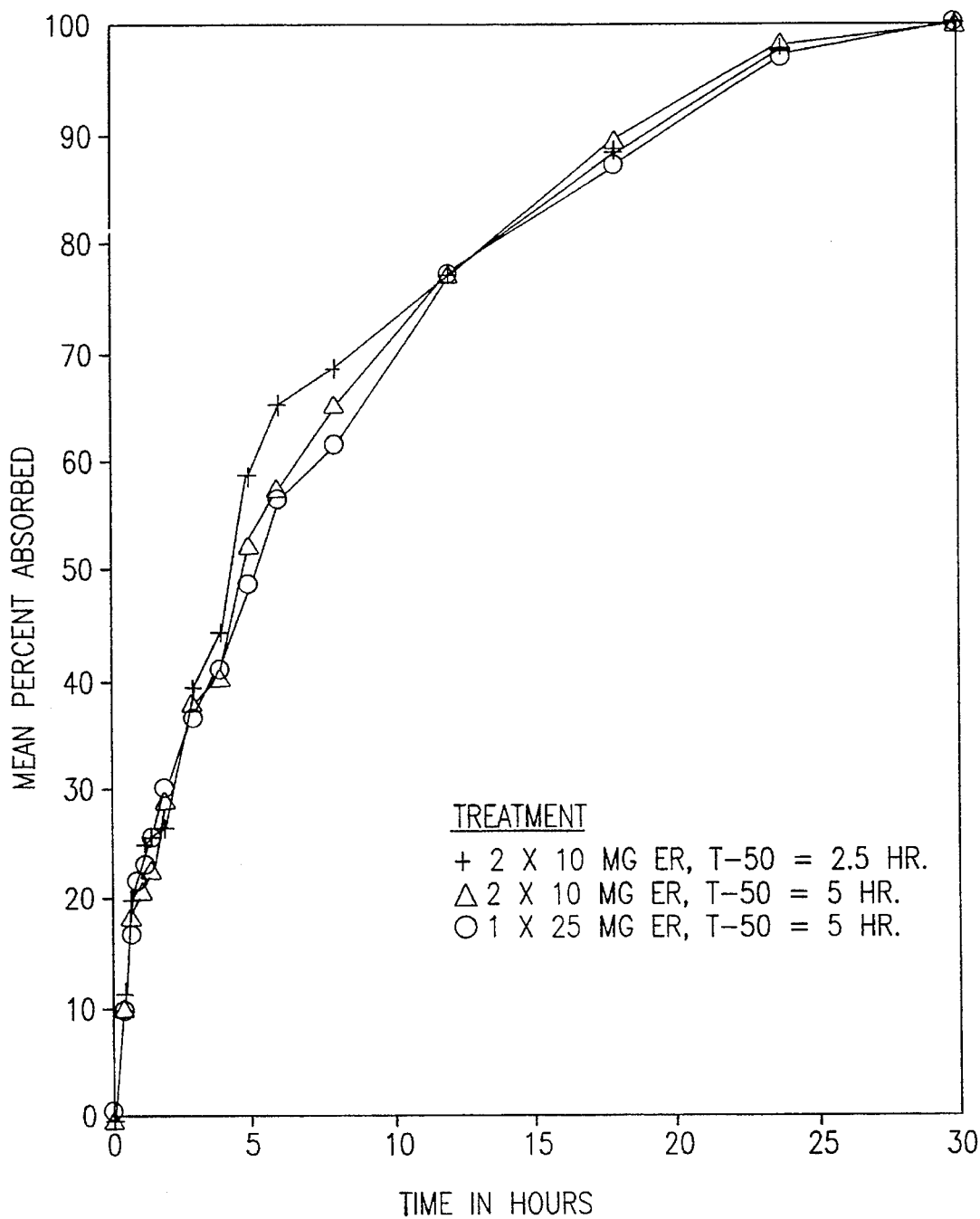
FIG. 4 indicates plots of mean percent gepirone absorbed in vivo vs time after ER administration, for the treatments recited.

FIG. 4 demonstrates that gepirone is absorbed continuously from the ER dosage form well beyond 24 hours. Thus, absorption and in vivo delivery for up to 30 hours can be attained using gepirone ER. On average, about 18 to about 24 hours was required to attain about 90 to about 95% absorption of gepirone from the ER formulation.

Also, FIG. 4 shows that there is no premature release or "dose dumping" of gepirone from the ER formulation. For T-50 values of 2.5 or 5 hours, oral gepirone ER is absorbed at about the same rate when administered in 20 and 25 mg doses.

The gepirone ER composition and dosage forms of the invention are designed to deliver an effective anxiolytic amount of gepirone or a pharmaceutically acceptable salt thereof to a mammal, preferably a human patient.

Effective doses of about 0.01 to 40 mg/kg body weight are contemplated. For certain central nervous system disorders, 15 to 90 mg/day, preferably 30–60 mg/day, are recommended. See U.S. Pat. No. 4,771,053 to Cott et al.

The invention deals exclusively with the administration of gepirone and its salts via orally-ingested dosage forms. Thus tablets, capsules, caplets, lozenges, powders, suspensions, syrups and the like are suitable forms. The use of tablets is preferred.

Applicants have found that the dissolution properties of their gepirone hydrochloride compositions are enhanced when they are administered via tablets having a convex shape. Such tablets can be made using a tablet press equipped with concave tablet tooling.

Spherical, i.e., round, tablets and capsule-shaped tablets were effective, but are less preferred.

The oral compositions may contain a variety of conventional pharmaceutically acceptable excipients in effective amounts suitable for their respective functions. Thus, suitable amounts of conventional additives, such as the following, are useful: polymeric matrixes (e.g. chitosan, hydroxyalkylcelluloses), auxiliary binding agents (e.g. syrup, acacia, gelatin, sorbitol, tragacanth, or polyvinyl pyrrolidone), fillers (e.g. lactose, sugar, maize-starch, calcium phosphate, sorbitol or glycine), lubricants (e.g. magnesium stearate, cellulose, talc, polyethyleneglycol or silicas), disintegrants (e.g. starch), wetting agents (e.g. sodium lauryl sulfate), colorants (e.g. iron oxides), etc. Mixtures of agents of these types can be used.

Generally, the compositions of the invention will contain from about 0.5 to about 12.0 wt % of the active pharmaceutical agents and from about 99.5 to about 88.0 wt % of combinations of sustaining agents and other excipients.

For oral formulations and dosage forms, the use of a polymeric cellulose matrix, or sustaining agent, is preferred. Suitable matrixes include hydroxyalkylsubstituted alkylcelluloses having viscosities of about 15,000 cps to about 100,000 cps. Hydroxymethyl propylcellulose (HPMC) of grades K15M and K100M (i.e., 15,000 and 100,000 cps, respectively) are highly preferred.

The replacement of some or all of the HPMC matrix with dicalcium phosphate or lactose generally increases dissolution rates.

Preferred oral formulations contain gepirone hydrochloride (gepirone HC1) and are administered as tablets having hardnesses of about 12 to about 25 SCU, with 16 SCU most preferred.

By "total colorant" applicants mean the sum of the concentrations of all colorants used in a formulation.

PREFERRED EMBODIMENTS

Unless stated otherwise, all percentages recited herein are weight percents, based on total composition weight. All disclosures referred to herein are hereby incorporated by reference.

Processing Procedure

The compositions of several dosage forms made are shown in Tables 1 and 3, infra. The gepirone HCl was made in accordance with procedures described in U.S. Pat. No. 4,423,049. The hydroxypropyl methylcellulose (HPMC) is the dissolution sustaining agent. The iron oxides were the colorants, colloidal silicon dioxide was the glidant, microcrystalline cellulose (MCC) is the compressibility aid (or binder) and magnesium stearate is the tabletting lubricant.

The following scheme is a flow chart for the production of gepirone ER blends:

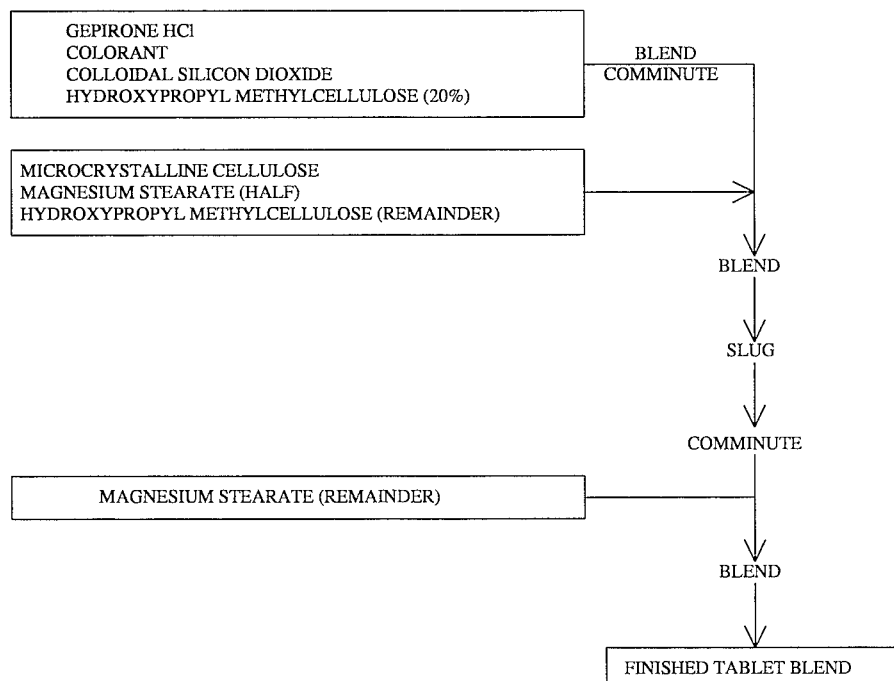

The resultant blends are then directly compressed into tablets or made into micropellets. If micropellets are made, they are option overcoated with conventional coating adjuvant(s) and then tableted or filled into capsules.

EXAMPLES

Example 1 summarizes comparative studies of the properties of gepirone ER and gepirone IR dosage forms. The extended release (ER) compositions and dosage forms therein are useful in accordance with the invention.

Example 2 shows useful formulations and dosage forms made according to the invention.

Example 1:

Twelve healthy, male subjects, ranging in age from 19 to 36 years (mean±standard deviation of 24.1±6.0 years) and weight from 56.6 to 86.0 kg (mean+ standard deviation of 72.8±9.7 kg), participated in the study after signing an informed consent form.

The formulations indicated in Table I were used in these tests.

TABLE 1

Compositions Tested in Human Subjects

| | E.R. | | | I.R. |
|---|---|---|---|---|
| | 1 | 2 | 3 | 4 |
| Gepirone HCl (mg) | 10 | 10 | 25 | 5 |
| HPMC (mg) | 187.4 | 280.0 | 290.0 | — |
| Cellulose (mg) | 40.0 | 56.0 | 61.0 | 122.0 |
| SiO$_2$ (mg) | 1.0 | 1.6 | 1.6 | — |
| Magnesium stearate (mg) | 1.6 | 2.4 | 2.4 | 1.3 |
| Lactose (mg) | — | — | — | 375.7 |
| Sodium starch glycolate (mg) | — | — | — | 17.0 |

This was an open, randomized, 4-session crossover study balanced for first order residual effects. Each session was separated by a 7-day washout period. All the subjects received, in an order determined from the rows of a 4×4 Latin square, a single 20 mg dose of ER gepirone (2×10 mg tablet with T-50=2.5 hours; Treatment 1), a single 20 mg dose of ER gepirone (2×10 mg tablet with T-50=5.0 hours; Treatment 2), a single 25 mg dose of ER gepirone (1×25 mg tablet with T-50=5.0 hours; Treatment 3), or 10 mg IR gepirone capsule given every 12 hours (i.e., q12h) (2×5 mg capsules; Treatment 4). All doses of gepirone were administered with 200 ml of water.

Blood samples were taken pre-dose, at 0.25 hour intervals for the first hour and a half, and then hourly. The 12 hour sample was taken prior to the administration of the evening IR dose.

Plasma was separated and samples were assayed for gepirone and 1-PP using a validated gas chromatographic-mass spectrometric (GC-MS) method similar to that reported for buspirone. See Sciacca et al, "Simultaneous Quantitation of Buspirone and 1-(2-Pyrimidinyl)-piperazine in Human Plasma and Urine by Capillary Gas Chromatography-Mass Spectrometry," *J. Chromatog.*, 428:265–274 (1988).

The following parameters were calculated by methods disclosed in Gibaldi et al in *Pharmacokinetics*, 2nd Ed., pp. 409–471, (1982); Marcel Dekker, Inc., New York; and Reigelman et al in "The Application of Statistical Moment Theory to the Evaluation of in vivo Dissolution Time and Absorption Time," *J. Pharmacokin. Biopharm.*, 8; 509–534 (1980): maximum plasma concentration (Cmax) and its corresponding time (Tmax), the area under the plasma concentration-time curve from time zero to 30 hours (AUC$_{0-30}$) and from time zero to infinity (AUC$_{inf}$), and the elimination half-life (T½). Cmax and Tmax were recorded from observed data. The terminal elimination rate constants ($\beta$) were estimated from the slope of the best fit terminal log-linear portion of the plasma concentration-time curve. The elimination T½ was estimated by dividing 0.693 by $\beta$. The AUC to the last measurable time point was calculated by a combination of linear and log-linear trapezoidal rule, and extrapolated to infinity.

Evaluation of absorption kinetics for gepirone was carried out using the method described by Wagner and Nelson in, "Kinetic Analysis of Blood Levels and Urinary Excretion in the Absorptive Phase after Single Doses of Drug," *J. Pharm. Sci.*, 53:1392–1403 (1964).

The fraction of gepirone absorbed as a function of time ($F_T$) was computed for each subject as follows:

$$(F_T)=[(C_T/k+AUC_{0-T})/AUC_{inf}]\times 100$$

In the numerator, $C_T$ is the concentration of gepirone at time, T, and k is the elimination rate constant obtained from treatment 4 (IR formulation) calculated using noncompartmental methods. In the denominator, AUC$_{inf}$ us calculated as:

$$AUC_{inf}=AUC_{0-T}+C_T/k$$

where k is the elimination rate constant from treatment 4.

The results are calculated for individual subjects and plotted as mean plasma concentration (ng/ml) or mean cumulative percent of drug absorbed versus time. See FIGS. 1 through 4.

FIG. 4 clearly shows that the oral gepirone ER formulations release the pharmaceutical agent at a rate such that about 18 to about 24 hours are required for about 90% of the agent to be absorbed.

Example 2:

Formulations A-I, set out in Table 2, have been made into tablets for oral administration. Table 3 shows concentration ranges for all of the ingredients employed in the tablets.

These tablets were made as described infra.

TABLE 2

Tabletted Gepirone HCl Formulations

| Ingredient | Mg. per tablet (wt %) | | | | | | | | |
| --- | --- | --- | --- | --- | --- | --- | --- | --- | --- |
| | A | B | C | D | E | F | G | H | I |
| Gepirone HCl | 2.0 | 5.0 | 20.0 | 10.0 | 5.0 | 10.0 | 20.0 | 2.0 | 40.0 |
| | (0.59) | (1.45) | (5.33) | (2.86) | (1.45) | (2.86) | (5.33) | (0.58) | (10.67) |
| HPMC *(100,000 cps) | 280.0 | 280.0 | 290.0 | 280.0 | 280.0 | 280.0 | 290.0 | 280.0 | 290.0 |
| | (82.1) | (82.2) | (77.3) | (80.0) | (81.2) | (80.0) | (77.3) | (81.9) | (77.3) |
| Microcrystalline cellulose NF | 56.2 | 56.7 | 61.8 | 56.6 | 56.3 | 56.3 | 61.3 | 56.3 | 41.3 |
| | (16.5) | (16.4) | (16.5) | (16.2) | (16.3) | (16.1) | (16.3) | (16.5) | (11.0) |
| Colloidal silicon dioxide | 1.6 | 1.6 | 1.6 | 1.6 | 1.6 | 1.6 | 1.6 | 1.6 | 1.6 |
| | (.5) | (.46) | (.42) | (.46) | (.46) | (.46) | (.43) | (.47) | (.43) |
| Magnesium stearate | 1.2 | 1.2 | 1.2 | 1.2 | 1.2 | 1.2 | 1.2 | 1.2 | 1.2 |
| | (.35) | (.35) | (.32) | (.34) | (.35) | (.34) | (.32) | (.35) | (.32) |
| Yellow ferric oxide | 0 | 0.5 | 0 | 0.4 | 0.5 | 0.5 | 0.5 | 0.5 | 0.5 |
| | | (.14) | | (.11) | (.15) | (.14) | (.13) | (.15) | (.13) |
| Red iron oxide pigment | 0 | 0 | 0.4 | 0.2 | 0.4 | 0.4 | 0.4 | 0.4 | 0.4 |
| | (0) | (0) | (.11) | (.06) | (.12) | (.11) | (.11) | (.12) | (.11) |

*HPMC = hydroxypropyl methylcellulose K100M, 2208 CR grade (Dow Chemical, Midland, Mich.)

TABLE 3

| Concentration Ranges | | |
| --- | --- | --- |
| Ingredient | Parts | wt % |
| Gepirone HCl | 2.0 to 40.0 | 0.50–12.0, pref. 0.5–11 |
| HPMC | 280.0–290.0 | 70.0–85.0, pref. 77.0–83.0 |
| Microcrystalline Cellulose | 40.0–62.0 | 10–20, pref. 11–16.5 |
| Colloidal silicon dioxide | 1.0–3.0 | 0.3–0.4, pref. 0.4–0.5 |
| Yellow ferric oxide | 0.3–0.6 | 0–0.5, pref. 0–0.15 |
| Red iron oxide | 0.1–0.5 | 0–0.5, pref 0–0.4 |
| Magnesium stearate | 1.0–7.5 | 0.31.0, pref. 0.30.4 |

Typical procedures for making tablets are:

PROCEDURE A

A blend was made of the colloidal silicon dioxide, along with the optional yellow/red colorant(s), the gepirone HCl and approximately 20% of the hydroxypropyl methylcellulose for 5 minutes in a 140 quart Hobart planetary mixer set at speed setting No. 1 was satisfactory for a 330,000 to 350,000 tablet batch. The blend was milled to deagglomerate, by passing it through a fitzmill equipped with a #000 plate, impact forward operating at high speed.

The milled material was mixed with the remaining hydroxypropyl methylcellulose, the microcrystalline cellulose and half the magnesium stearate. This mix was blended in a Lodige Model FKM-600 mixer at 75 rpm with the chopper off for 3 minutes. The blend was slugged with a 1 ¼" flat-faced tooling on a Colton250 tablet press. Slugging the blend with a ⅝" flat-faced tooling on a Stokes BB2 tablet press was satisfactory for a 1.05 million tablet batch. The slugs were then passed through a Fitzmill equipped with a #2A plate, knives forward operating at medium speed.

The milled material was blended with the remaining magnesium sterate in a Lodige Model FKM-600 mixer with the chopper off at 75 rpm for about 2 to 3 minutes. The finished blend was compressed into tablets.

Formulations A-H were made using Procedure A, which is preferred.

PROCEDURE B

Sample I was prepared using a procedure similar to that above. However, preparation varied in that: (1) the entire blending step took place in a 20 quart planetary mixer to yield a 69,000 tablet batch; (2) the blending of the deagglomerated material with the remaining HPMC, cellulose and half the magnesium sterate took place in a Lodige Mode FM-100 mixer at 120 rpm, for 3 minutes with the chopper off; (3) the blend was slugged with a ⅝" flat-faced, beveled edge tooling on a monesty B3B tablet press; and (4) the final addition of magnesium stearate was made via blending in a Lodige Model FM-100 with the chopper off at 120 rpm for 3 minutes.

Procedure B is an effective method of making tablet blends.

Reasonable variations, such as those which would occur to one of ordinary skill in the art, can be made herein without departing from the scope of the invention.

We claim:

1. A pharmaceutical composition useful for making an oral extended release gepirone dosage form comprising:
   (a) from about 0.5 to about 12.0 wt % gepirone hydrochloride;
   (b) from about 70 to about 85 wt % of a pharmaceutically acceptable cellulosic polymer matrix; and
   (c) suitable amounts of one or more pharmaceutically acceptable excipients, wherein the release rate of gepirone from the dosage form is such that about 18 to 24 hours are required to attain from about 90 to about 95% absorption of gepirone.

2. The composition of claim 1 wherein (c) includes at least one of: colorant, microcrystalline cellulose, colloidal silica and magnesium stearate.

3. The composition of claim 2 wherein (b) is hydroxypropylmethylcellulose having a viscosity of from about 15,000 cps to about 100,000 cps.

4. The composition of claim 3 consisting essentially of:
   (a) from about 0.5 to about 11.0 wt % gepirone hydrochloride;
   (b) from about 72.0 to about 83.0 wt % hydroxypropylmethylcellulose;

(c) about 01 to about 0.7% total colorant;
(d) about 10.0 to about 20.0% microcrystalline cellulose;
(e) about 0.3 to about 0.6% colloidal silica; and
(f) about 0.3 to about 1.0% magnesium stearate.

5. The composition of claim 4 containing:
(a) about 5.3 wt % gepirone hydrochloride;
(b) about 77.3 hydroxypropylmethylcellulose having a viscosity of about 100,000 cps;
(c) from about 0.1 to about 0.2% iron oxide pigments;
(d) about 16.5% microcrystalline cellulose;
(e) about 0.4% colloidal silica; and
(f) about 0.3% magnesium stearate.

6. An oral dosage form comprising the pharmaceutical composition of claim 5.

7. The composition of claim 4 containing:
(a) about 2.7 wt % gepirone hydrochloride;
(b) about 80.0% hydroxypropylmethylcellulose, having a viscosity of about 100,000 cps;
(c) from about 0.6 to about 0.9% total colorant;
(d) about 0.4% colloidal silicon; and
(f) about 0.3% magnesium stearate.

8. An oral dosage form comprising the composition of claim 7.

9. An improved method for administering gepirone comprising oral administration of a dosage form made from the composition of claim 1.

10. An improved method for administering gepirone comprising oral administration of a dosage form made from the composition of claim 5.

11. An improved method for administering gepirone comprising oral administration of a dosage form made from the composition of claim 7.

12. An oral dosage form comprising micropellets of the composition of claim 1, which micropellets are tableted or filled into capsules.

13. The dosage form of claim 12 wherein the micropellets are overcoated with a pharmaceutically acceptable coating adjuvant.

14. An oral dosage form comprising direct compressed tablets of the composition of claim 1.

15. An oral dosage form comprising directly compressed tablets of the composition of claim 5.

16. An oral dosage form comprising directly compressed tablets of the composition of claim 7.

* * * * *